United States Patent [19]

Catt et al.

[11] 4,419,358

[45] Dec. 6, 1983

[54] ISETHIONIC ACID SALT OF 9-CYCLOHEXYL-2-PROPOXY-9H-PURINE-6-AMINE AND COMPOSITIONS CONTAINING AN EFFECTIVE BRONCHODILATING CONCENTRATION OF IT

[75] Inventors: John D. Catt; Davis L. Temple, Jr., both of Evansville, Ind.

[73] Assignee: Mead Johnson & Company, Evansville, Ind.

[21] Appl. No.: 320,357

[22] Filed: Nov. 12, 1981

[51] Int. Cl.³ .................... A61K 31/52; C07D 473/18
[52] U.S. Cl. .................................... 424/253; 544/276
[58] Field of Search ........................ 424/253; 544/276

[56] References Cited

U.S. PATENT DOCUMENTS

| | | | |
|---|---|---|---|
| 4,057,686 | 11/1977 | Fiecchi | 536/26 |
| 4,172,829 | 10/1979 | Naito et al. | 424/253 |
| 4,232,155 | 11/1980 | Naito et al. | 544/277 |
| 4,278,675 | 7/1981 | Naito et al. | 424/253 |
| 4,286,093 | 8/1981 | Temple, Jr. | 544/276 |

*Primary Examiner*—Diana G. Rivers
*Attorney, Agent, or Firm*—Richard P. Ryan; Robert H. Uloth

[57] ABSTRACT

This invention concerns an isethionic acid addition salt of the non-adrenergic bronchodilating agent 9-cyclohexyl-2-propoxy-9H-purine-6-amine. The salt is comprised of a 2:1 molecular ratio of the isethionic acid to the adenine base. The salt of the invention is characterized in having improved water solubility and stability.

4 Claims, No Drawings

ISETHIONIC ACID SALT OF 9-CYCLOHEXYL-2-PROPOXY-9H-PURINE-6-AMINE AND COMPOSITIONS CONTAINING AN EFFECTIVE BRONCHODILATING CONCENTRATION OF IT

BACKGROUND OF THE INVENTION

This invention covers the acid addition salt of 9-cyclohexyl-2-propoxy-9H-purine-6-amine with 2-hydroxyethanesulfonic acid (isethionic acid) having an acid to base molecular ratio of 2:1. The compound of this invention is classified in general as a drug, bioaffecting and body-treating type of compound. The base component of the subject salt is referred to herein by code number MJ 13156 and is represented by the following structural formula.

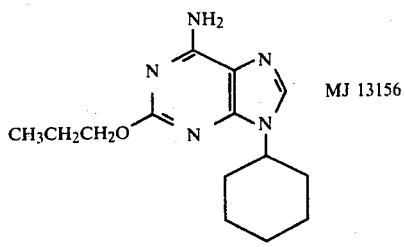

MJ 13156

Naito, et al., U.S. Pat. No. 4,172,829 patented Oct. 30, 1979 describes preparation of MJ 13156, its use as a non-adrenergic bronchodilator and conversion to pharmaceutically acceptable acid addition salt by conventional methods. The term "pharmaceutically acceptable acid addition salts" as used therein included those salts formed from mineral acids such hydrochloric, hydrobromic, hydroiodic, nitric, sulfuric, phosphoric, and the like; and also organic acids such as acetic, citric, pivalic, lactic, tartaric, oxalic, succinic, maleic, and the like. The conventional method disclosed for preparing the acid addition salts involved dissolving the free base in an inert solvent, and reacting it with about one equivalent weight of a suitable organic or inorganic acid to produce the desired salt, and recovering the salt by solvent precipitation or lyophilization. These conventional pharmaceutically acceptable acid addition salts of MJ 13156 are not well suited for present use due to limited solubility and, in some cases, lack of stability.

When a substance is employed for medical purposes, it is recognized that solubility of the therapeutic agent often is the controlling factor in determining route of administration and dosage forms. For instance, a water soluble substance can be generally administered intravenously whereas a water insoluble material is limited to other forms of parenteral administration such as intramuscular and subcutaneous routes. Additionally, therapeutic agents having water solubility also facilitate the preparation of various oral and topical dosage forms for human administration. Accordingly, the prime objective of the present invention was to provide a water soluble, stable, therapeutically acceptable form of the bronchodilator agent MJ 13156 which could be administered by several routes, e.g., orally, intravenously, and topically.

SUMMARY AND DETAILED DESCRIPTION OF THE INVENTION

This invention is concerned with the acid addition salt comprised of MJ 13156 and isethionic acid in which the acid to base molecular ratio comprises a 2:1 ratio of equivalents of each.

More conventional pharmaceutically acceptable acid addition salts of MJ 13156 are not well suited for the present use due to a limited solubility and, in some cases, lack of stability. The following table shows solubility data for some acid addition salts of MJ 13156 at room temperature (about 25° C.).

TABLE 1

| Acid | Salts of MJ 13156 Solubility (mg/mL) | Method[1] |
|---|---|---|
| hydrochloric | 1.4 | A |
| hydrobromic | 1.6 | B |
| sulfuric | 0.8 | B |
| nitric | 2.4 | B |
| phosphoric | 1.3 | B |
| methanesulfonic | 8.0 | A |
| isethionic | 100.0 | A |
| acetic | only formed a solvate | |
| levulinic | only formed a solvate | |
| gluconic | did not react | |
| lactobionic | did not react | |

[1]Solubility data obtained using one of two methods:
Method A
Solubilities of isolated salts determined in standard manner by adding H₂O to weighed salt samples and directly obtaining solubility data.
Method B
Solubilities of salts prepared in situ determined by adding a mole-equivalent of each acid to a 140 mg sample of MJ 13156 and then diluting with H₂O in increments to 2.5 mg/mL. A second mole-equivalent of acid was added to each sample and allowed to stand overnight. The precipitates were collected, dried, and weighed to obtain the solubility data.

As inspection of Table 1 will demonstrate, the mineral acids give salts with only limited water solubility. The methanesulfonate salt has reasonable water solubility but dissociates moderately in water. Attempts were made to prepare salts using gluconic, lactobionic, acetic, and levulinic acids; however, MJ 13156 is too weak a base to form a salt with these acids. Although acetic acid and levulinic acid did give a complex with MJ 13156 that contained the acid molecule, nevertheless, these were not salts but were merely solvates that dissociated in water to give MJ 13156 base. Spectral analysis (NMR and IR) of the acetic acid solvate was consistent for MJ 13156 free base and free acetic acid. The isethionate salt is clearly the most soluble of all those prepared. The unusual feature of this salt is that it consists of 2 moles of acid to 1 mole of the base; a feature perhaps accounting for the solubility of the salt. Attempts to form the mono salt by adding base to an aqueous solution of the isethionate salt resulted in precipitation of MJ 13156 base before one full equivalent of base was added. Preparation of the isethionate salt of MJ 13156 is carried out by treating an equivalent of base in ethyl acetate with 2 equivalents of isethionic acid in ethanol-ethyl acetate solution. Chilling the mixture yields the salt which is collected by filtration. The salt can similarly be prepared by using more concentration solutions of both the acid and the base in ethanol. When wet ethanol is used, a hydrate is obtained.

Administration of the instant salt may be done by methods outlined in the aforementioned U.S. Pat. No. 4,172,829 of Naito, et al., incorporated herein in its entirety by reference. Additionally, solutions of the instant salt containing a salt concentration of 5% or less weight to volume may be used for topical administration. These solutions may also contain preservatives such as methylparabens, propylparabens, phenylethyl alcohol, or benzyl alcohol; buffers such as citrate, phosphate, acetate; chelating agents such as ethylenediamine, tetraacetic acid salts, bis-(2-hydroxyethyl)glycine, and tartaric acid; and antioxidants such as sodium bisulfite, ascorbic acid, and cysteine hydrochloride. These pharmaceutical additives are frequently used in products of this type. A typical solution for nebulization can be prepared by dissolving drug (1 gram equivalent), chlorbutanol (5 g), and propylene glycol (50 g) in water to give 1000 mL solution which is filtered and packaged.

The isethionic acid salt of MJ 13156 may also be administered using other dosage forms. This salt can be dissolved or suspended in a halocarbon or hydrocarbon propellant system and packaged in a metered dose aerosol container. Cosolvents or surfactants and suspending agents may also be included in this dosage form. Typically, appropriate pressurized containers fitted with metering valves and an actuator with a 50 mg metering chamber (to deliver 1 mg drug) are filled with a mixture comprising 20 g micronized drug, 245 g $Cl_2F_2C$, and 735 g $Cl_2F_4C_2$. The salt can also be administered as a powder for insufflation, consisting of a blend of inert powder ingredients admixed with an appropriate amount of the isethionate salt of appropriate particle size, administered by a powder insufflation device. Generally, 1 part micronized drug is blended with 50 parts USP lactose having appropriate microbial properties. This blend is encapsulated for use in a suitable insufflation device. Prior to use, the capsule must be punctured or opened to allow release of the powder blend.

DESCRIPTION OF SPECIFIC EMBODIMENTS

The following non-limiting examples will serve to illustrate the invention.

EXAMPLE 1

Preparation of MJ 13156
9-Cyclohexyl-2-propoxy-9H-adenine

A solution of 2.21 g (7.8 mmoles) of 9-(2-cyclohexenyl)-2-propoxy-9H-adenine in 30 mL of 90% ethanol was hydrogenated overnight with 250 mg of 10% palladium on carbon and then filtered. The filtrate was evaporated in vacuo, giving a residue which was crystallized from ethyl acetate—n-hexane. Yield 1.85 g (76%); melting point 148°–150° C.

Anal. Calcd. for $C_{14}H_{21}N_5O$: C, 61.07; H, 7.69; N, 25.43. Found: C, 61.07; H, 7.89; N, 25.48.

The procedure given above for preparation of MJ 13156 base was outlined in the earlier cited Naito, et al. patent (specifically Example 2) incorporated herein by reference.

EXAMPLE 2

Preparation of MJ 13156 Isethionate Salt
9-Cyclohexyl-2-propoxy-9H-purine-6-amine
2-Hydroxyethanesulfonate To a solution of 1.84 g (0.015 mole) isethionic acid in 3 mL dry ethanol and 20 ml ethyl acetate, 2.00 g (0.007 mole) MJ 13156 base in 50 ml ethyl acetate was added rapidly. The mixture was cooled and the solid collected on a filter to give 3.8 g of white solid, melting point 142.5°–143.5° C.

Anal. Calcd. for $C_{14}H_{21}N_5O.2C_2H_6O_4S$: C, 40.98; H, 6.31; N, 13.27. Found: C, 41.00; H, 6.34; N, 12.98.

NMR (DMSO-$d_6$): chemical shift (no. protons, multiplicity)—0.98 (3,t); 1.36 (2,m); 1.83 (10,m); 2.79 (4,t, J=7.0 Hz); 3.69 (4,t, J=7.0 Hz); 4.36 (3,m); 8.66 (1,s); 9.10 (6,br s).

IR (KBr): 740, 810, 1050, 1195, 1310, 1620, 1700, 2650, 2935, and 3240 cm$^{-1}$.

With wet ethanol a hydrate is obtained.

Anal. Calcd. for $C_{14}H_{21}N_5O.2C_2H_6O_4S.H_2O$: C, 39.62; H, 6.47; N, 12.84. Found: C, 40.00; H, 6.14; N, 12.70.

What is claimed is:

1. The di-2-hydroxyethanesulfonate salt of 9-cyclohexyl-2-propoxy-9H-purine-6-amine (I)

2. The salt of claim 1 in dilute solution suitable for bronchial application comprising a liquid pharmaceutical carrier containing an effective bronchodilating concentration of said salt.

3. The salt of claim 1 admixed in effective bronchodilating concentration with a suitable propellant system and packaged for aerosol administration.

4. The salt of claim 1 as a powder for insufflation comprising a blend of inert ingredients acceptable for insufflation admixed with said salt, said inert ingredients and said salt having appropriate particle size for transport into the bronchioles following insufflation.

* * * * *